US010527587B2

(12) United States Patent
Su et al.

(10) Patent No.: US 10,527,587 B2
(45) Date of Patent: Jan. 7, 2020

(54) DISTRIBUTED SENSING FIBER ACOUSTIC EMISSION APPARATUS AND METHOD FOR MONITORING HYDRAULIC ENGINEERING SAFETY BEHAVIOR

(71) Applicant: HOHAI UNIVERSITY, Nanjing (CN)

(72) Inventors: Huaizhi Su, Nanjing (CN); Meng Yang, Nanjing (CN)

(73) Assignee: HOHAI UNIVERSITY, Nanjing (CN)

( * ) Notice: Subject to any disclaimer, the term of this patent is extended or adjusted under 35 U.S.C. 154(b) by 99 days.

(21) Appl. No.: 15/831,469

(22) Filed: Dec. 5, 2017

(65) Prior Publication Data
US 2019/0170697 A1 Jun. 6, 2019

(51) Int. Cl.
*G01N 29/14* (2006.01)
*G01N 29/22* (2006.01)
*G01N 29/24* (2006.01)
*G01H 9/00* (2006.01)

(52) U.S. Cl.
CPC .......... *G01N 29/14* (2013.01); *G01N 29/221* (2013.01); *G01N 29/225* (2013.01); *G01N 29/2418* (2013.01); *G01H 9/004* (2013.01); *G01N 2291/0232* (2013.01)

(58) Field of Classification Search
CPC .... G01N 29/14; G01N 29/221; G01N 29/225; G01N 29/21; G01H 9/004; G01M 3/38; G01M 3/047; G01M 3/04; G01M 3/103; G01M 3/16; G01M 3/002
See application file for complete search history.

(56) References Cited

U.S. PATENT DOCUMENTS

| | | | | |
|---|---|---|---|---|
| 4,654,520 A * | 3/1987 | Griffiths | ................. | G01B 11/18 250/227.14 |
| 5,663,490 A * | 9/1997 | Kozen | ................... | G01M 3/002 405/54 |
| 6,526,807 B1 * | 3/2003 | Doumit | .................... | G01M 3/04 340/605 |
| 6,611,368 B1 * | 8/2003 | Grant | ................. | H04B 10/2916 359/334 |
| 6,885,498 B2 * | 4/2005 | Islam | ...................... | H01S 3/302 359/334 |
| 7,355,716 B2 * | 4/2008 | de Boer | ............... | A61B 5/0059 356/479 |
| 7,412,129 B2 * | 8/2008 | Yalin | ..................... | F02D 35/022 385/31 |
| 7,418,169 B2 * | 8/2008 | Tearney | ............. | A61B 1/00082 385/11 |

(Continued)

*Primary Examiner* — Helen C Kwok
(74) *Attorney, Agent, or Firm* — Rankin, Hill & Clark LLP

(57) ABSTRACT

A distributed sensing fiber acoustic emission apparatus and method for monitoring a hydraulic engineering safety behavior includes a fiber-carrying laying module and a fiber acoustic emission module. The fiber-carrying laying module includes an inner supporter, mesh modules and fiber-carrying modules, the inner supporter, the mesh modules and the fiber-carrying modules form a cylindrical shape. The cross section of the inner supporter is in a quadrangle inner-concave shape with the four edges concaved, the four surfaces of the inner supporter are concaved, the mesh modules having a plurality of meshes are respectively disposed in the four concave surfaces of the inner supporter, and the fiber-carrying module is arranged between every two adjacent mesh modules.

7 Claims, 3 Drawing Sheets

(56) References Cited

U.S. PATENT DOCUMENTS

| | | | |
|---|---|---|---|
| 7,538,859 B2* | 5/2009 | Tearney | A61B 5/0066 356/35.5 |
| 2004/0113104 A1* | 6/2004 | Maida, Jr. | E21B 47/123 250/573 |
| 2009/0220190 A1* | 9/2009 | Zandiyeh | G01M 3/047 385/13 |
| 2018/0180510 A1* | 6/2018 | Su | G01K 11/32 |
| 2018/0195969 A1* | 7/2018 | Su | B23P 19/04 |

* cited by examiner

DISTRIBUTED SENSING FIBER ACOUSTIC EMISSION APPARATUS AND METHOD FOR MONITORING HYDRAULIC ENGINEERING SAFETY BEHAVIOR

TECHNICAL FIELD

The present invention relates to a distributed sensing fiber acoustic emission apparatus and method for monitoring a hydraulic engineering safety behavior, and belongs to the field of hydraulic engineering safety monitoring and detection.

BACKGROUND

As everyone knows, the optical wave is an electromagnetic wave; when the electromagnetic wave is emitted in a medium such as a fiber, the incident electromagnetic wave will interact with molecules or atoms forming the material, so as to generate scattering spectra, which commonly comprises Rayleigh scattering and Brillouin scattering. By using the scattered light information, people develop a lot of sensing fiber monitoring instruments, but regarding to the currently developed monitoring devices, the actual application of the fiber sensing technology lags far behind the requirement on the technology currently due of the variety of current performance parameters and the requirement of high standard, wherein the fusion sensing fiber technology and the acoustic emission technology are one of the fields lacking research.

In the hydraulic engineering and civil engineering, the interior of the material may have fractures of different degrees under the effects of external temperature, water loading, weight, etc. The fracture is invisible internal damage under many conditions, and if the fracture cannot be detected and found in time, it is possible to develop into a potential safety hazard in the engineering. This defect or damage may have a continuously accumulated and irreversible process with the time, which is possible to cause whole or partial sudden invalidation of the structure, so as to lead to serious engineering problem. The material may release elastic energy in damage, the elastic energy is transmitted in the form of elastic wave in the material, and the elastic wave is called acoustic emission wave.

In order to better guarantee the engineering safety and increase the reliability and stability of the system, it is very important to reduce unnecessary lose and cost, and explore a more advanced detecting and monitoring technology. Since the sensing fiber technology and the acoustic emission technology have good monitoring and detecting performance, the fusion thereof will generate great technical improvement. In order to break through the piezoelectric ceramic acoustic emission detection method with large system, many cables and bad anti-electronic logging interference ability and the current fiber bragg grating acoustic emission testing system of point mode monitoring, the present invention fuses the femtosecond laser optical frequency comb technology and acoustic emission technology, and realizes the monitoring and detecting technology with spatial orientation, whole-course distribution, high spatial resolution and high detecting precision through establishing the new type monitoring and detecting technology fusing the fiber sensing technology of Rayleigh scattering and Brillouin scattering, and the acoustic emission technology. The apparatus and the method have novel setting point, simple structure arrangement, convenient operation and good practical engineering application meaning and scientific researching value.

SUMMARY

Object of Invention in order to overcome the defects in the prior art, the present invention provides a distributed sensing fiber acoustic emission apparatus and method for monitoring a hydraulic engineering safety behavior. The present invention fuses the fiber acoustic emission module, a converter connection module and the fiber-carrying laying module, discloses combination of a femtosecond laser optical frequency comb technology and an acoustic emission technology, and establishes the monitoring apparatus and method for multi-stage time delay and multi-acoustic wave vibration frequency with allowance of spatial orientation, whole-course distributed detection, quantitative detection, multi-level physical size, and multi-acoustic emission wave resonance hole, and has great practical engineering application and scientific researching value.

Technical solution: in order to solve the technical above, a distributed sensing fiber acoustic emission apparatus for monitoring a hydraulic engineering safety behavior according to the present invention comprises a fiber-carrying laying module and a fiber acoustic emission module, wherein the fiber-carrying laying module comprises an inner supporter, mesh modules and fiber-carrying modules, the inner supporter, the mesh modules and the fiber-carrying modules form a cylindrical shape, the cross section of the inner supporter is in a quadrangle inner-concave shape with the four edges concaved, the four surfaces of the inner supporter are concaved, the mesh modules having a plurality of meshes are respectively disposed in the four concave surfaces of the inner supporter, and the fiber-carrying module is arranged between every two adjacent mesh modules;

the fiber acoustic emission module comprises a driving power source, a mode-locked laser, a femtosecond laser optical frequency comb, a pulse modulator, a wavelength division multiplexer, an optical path coupler, an amplifier, a receiver, a detector, a controller, a concrete structure safety behavior evaluation system, an acoustic emission signal, a Rayleigh optical receiver, a Brillouin optical receiver, and an optical splitter, the output end of the driving power source is connected with the input end of the mode-locked laser, the input end of the driving power source is connected with the output end of the controller, the mode-locked laser is connected with the femtosecond laser optical frequency comb, the pulse modulator and the wavelength division multiplexer in sequence, the output end of the wavelength division multiplexer is respectively connected with the input end of the optical splitter and the input end of the optical path coupler, the output end of the optical splitter is respectively connected with the input end of the Rayleigh optical receiver and the input end of the Brillouin optical receiver, the output end of the Rayleigh optical receiver and the output end of the Brillouin optical receiver are connected with the input end of the controller, the output end of the optical path coupler is connected with the input end of the amplifier and the input end of the receiver, and output end of the receiver is connected with the input end of the detector, the output end of the detector is connected with the input end of the controller, the output end of the amplifier is connected with a sensing fiber in the fiber-carrying laying module, and the output end of the controller is connected with the concrete structure safety behavior evaluation system.

Preferably, the mesh module comprises a carrier, the carrier is provided with meshes along an axis of the sensing fiber, each carrier is provided with one of a triangle common cavity mesh, a circular common cavity mesh, a quadrangle common cavity mesh and a pentagon common cavity mesh, the shapes of the meshes the carriers are different, and the triangle common cavity mesh, the circular common cavity mesh, the quadrangle common cavity mesh and the pentagon common cavity mesh are arranged in an anticlockwise order.

Preferably, the fiber-carrying module comprises a barrier block, sealing plugs, a double-fiber channel and a semicircular fiber bearing platform, the semicircular fiber bearing platform is connected with the carrier and is internally provided with the double-fiber channel, the double-fiber channel is internally provided with two sensing fibers, the two sides of the top of the semicircular fiber bearing platform are respectively hinged with the sealing plug, and the two sealing plugs are locked through the barrier block.

Preferably, the semicircular fiber bearing platform is internally provided with a fiber separation wall for separating the two sensing fibers.

Preferably, the fiber separation wall is a vacuum insulation panel. The sealing plug rotates around the bending folded shaft, the double-fiber channel is fixed in the semicircular fiber bearing platform, after the sealing plugs are closed, the barrier block is arranged on the outer end of the fiber separation wall to seal the closing parts of the sealing plugs, and the main function of the fiber separation wall is to separate and block the heat transmission between two adjacent sensing fibers in the double-fiber channel to prevent the mutual temperature cross influence generated by two adjacent sensing fibers. Therefore, the fiber separation wall is made of vacuum insulation material.

Preferably, the distributed sensing fiber acoustic emission apparatus for monitoring a hydraulic engineering safety behavior further comprises a converter connection module, wherein the converter connection module comprises a first base and a second base, the first base is connected with a fold shaft epitaxial column through a first lantern ring, the second base is connected with the fold shaft epitaxial column through a second lantern ring, both the first lantern ring and the second lantern ring are provided with a locking apparatus, the upper end of the first base is provided with a first fiber-carrying bending hole, the upper end of the second base is provided with a second fiber-carrying bending hole, the fold shaft epitaxial column is provided with an inner through hole, the inner through hole is internally provided with a bending folded shaft, and the upper end surface of the bending folded shaft is provided with a fixing plug.

A running method of the distributed sensing fiber acoustic emission apparatus for monitoring a hydraulic engineering safety behavior above comprises the following steps of:

first step: establishing the distributed sensing fiber acoustic emission apparatus for monitoring a hydraulic engineering safety behavior composed of the fiber acoustic emission module, the converter connection module and the fiber-carrying laying module, removing the barrier block, rotating the sealing plugs at the two sides around the bending folded shaft, arranging eight sensing fibers in four double-fiber channel in pairs, closing the sealing plugs at the two sides around the bending folded shaft, pressing a joint of the sealing plugs, passing the barrier block through the upper end of the fiber separation wall, and fixing the closing parts of the sealing plugs at the two sides;

Second step: placing a component formed by the mesh modules and the fiber-carrying modules in the first fiber-carrying bending hole and the second fiber-carrying bending hole at the possibly bent position of the fiber-carrying laying module, rotating the bending folded shaft according to engineering demands, so as to drive the rotation of the first base and the second base, thus forming a certain included angle between the first fiber-carrying bending hole and the second fiber-carrying bending hole, and then inserting the fixing plug into the bending folded shaft, and fixing the bending folded shaft, thus fixing the angle between the first fiber-carrying bending hole and the second fiber-carrying bending hole;

third step: opening each component in the fiber acoustic emission module, and starting the driving power source through controlling the controller, thus stimulating the mode-locked laser to generate a femtosecond laser optical frequency comb, and modulating the femtosecond laser optical frequency comb through the pulse modulator, the wavelength division multiplexer and the optical splitter; and fourth step: an acoustic emission signal being generated when some part of the structure to be monitored is damaged, the acoustic emission signal transmitted through the pentagon common cavity mesh, the triangle common cavity mesh, the circular common cavity mesh and the quadrangle common cavity mesh being transduced into the sensing fiber of the fiber-carrying laying module according to different time and frequencies, and Rayleigh scattering light information and Brillouin scattering light information in the sensing fiber being affected, receiving and detecting the femtosecond laser optical frequency comb of the changed Rayleigh scattering light information and the changed Brillouin scattering light information through the Rayleigh optical receiver and the Brillouin optical receiver, then collecting the information into the concrete structure safety behavior evaluation system through the controller for analysis and research, and evaluating and analyzing the information like the damaged position and degree of the structure.

Beneficial effect: the distributed sensing fiber acoustic emission apparatus for monitoring a hydraulic engineering safety behavior according to the present invention introduces the femtosecond laser optical frequency comb technology to integrate with the acoustic emission technology, separates Rayleigh scattering and Brillouin scattering to sense the acoustic emission wave by levels, establishes the monitoring technology for multi-stage time delay and multi-acoustic wave vibration frequency with multi-level physical size, and multi-acoustic emission wave resonance hole of a triangle common cavity mesh, a circular common cavity mesh, a quadrangle common cavity mesh and a pentagon common cavity mesh, and has the advantages of allowance of spatial orientation, whole-course distribution, high spatial resolution, high detecting precision, and allowance of quantitative detection. The present invention finally establishes a new type monitoring and detection technology of new type distributed sensing fiber acoustic emission including the fiber acoustic emission module, the converter connection module and the fiber-carrying laying module. The present invention has complete structure, novel setting point, simple structure arrangement, convenient operation, may realize the process and automation application, and had great advantages on reducing monitoring cost, increasing monitoring precision, improving engineering practicability, etc.

DETAILED DESCRIPTION

Figure 1:
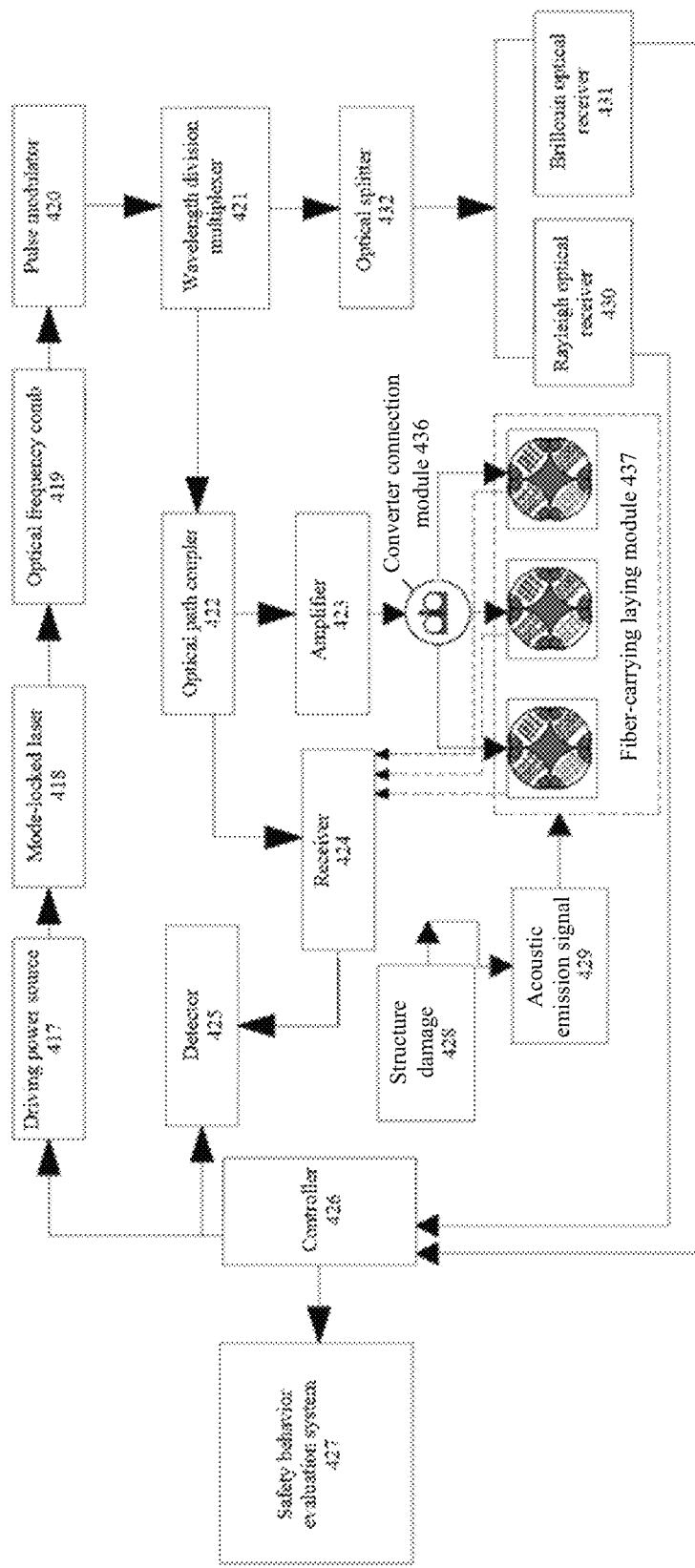
FIG. 1 is a structure diagram of the present invention.
Figure 2:
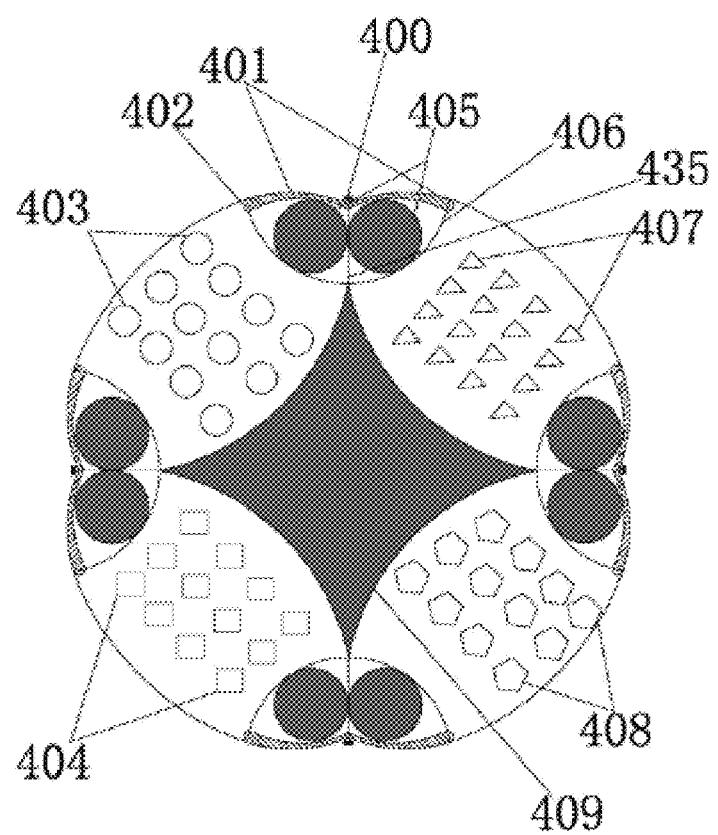
FIG. 2 is a structure diagram of a fiber-carrying laying module in FIG. 1.
Figure 3:
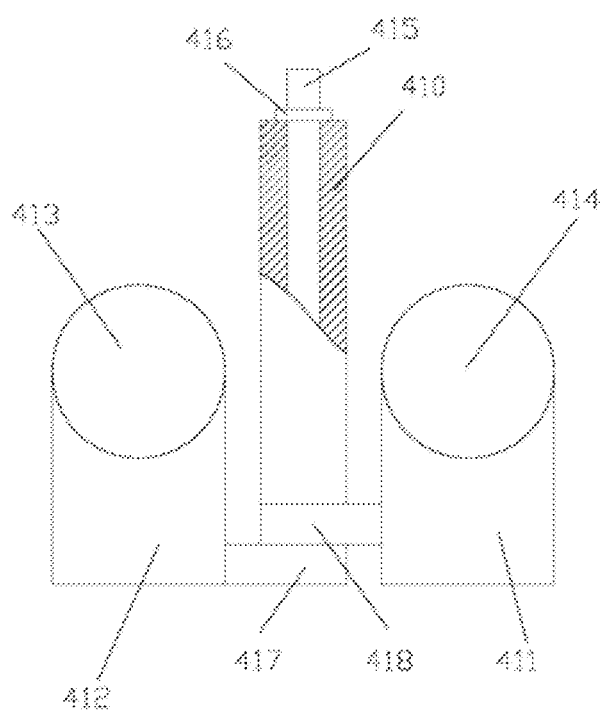
FIG. 3 is a structure diagram of a converter connection module in FIG. 1.

As shown in FIG. 1 and FIG. 3, a distributed sensing fiber acoustic emission apparatus for monitoring a hydraulic engineering safety behavior comprises a fiber acoustic emission module, a converter connection module and a fiber-carrying laying module, wherein the fiber acoustic emission module is connected with the fiber-carrying laying module, and the fiber-carrying laying module is connected with the converter connection module.

In the fiber acoustic emission module, the input end of the driving power source 417 is connected with the output end of the controller 426, the output end of the driving power source 417 is connected with the input end of the mode-locked laser 418, the output end of light information of the mode-locked laser 418 is connected with the femtosecond laser optical frequency comb 419, the output end of the femtosecond laser optical frequency comb 419 is connected with the input end of the pulse modulator 420, the output end of the pulse modulator 420 is connected with the input end of the wavelength division multiplexer 421, the input end of the wavelength division multiplexer 421 is respectively connected with the input end of the optical splitter 432 and the input end of the optical path coupler 422, the output end of the optical splitter 432 is respectively connected with the input end of the Rayleigh optical receiver 430 and the input end of the Brillouin optical receiver 431, the output end of the Rayleigh optical receiver 430 and the output end of the Brillouin optical receiver 431 are connected with the input end of the controller 426, the output end of the optical path coupler 422 is connected with the input end of the amplifier 423 and the input end of the receiver 424, the output end of the receiver 424 is connected with the input end of the detector 425, the output end of the detector 425 is connected with the input end of the controller 426, the output end of the amplifier 423 is connected with a GJJV tight-buffered sensing fiber in the fiber-carrying laying module 437, and the output end of the controller 426 is connected with the concrete structure safety behavior evaluation system 427.

In the embodiment, a fold shaft epitaxial column 410 with a height of 50 cm and a width of 5 cm is located at the middle position between a first base 412 with a bottom width of 30 cm and a second base 411 with a bottom width of 30 cm, the first base 412 is connected with a fold shaft epitaxial column 410 through a first lantern ring 417, the second base 411 is connected with the fold shaft epitaxial column 410 through a second lantern ring 418, both the first lantern ring 417 and the second lantern ring 418 are provided with a locking apparatus, the upper end of the first base 412 is provided with a first fiber-carrying bending hole 413 with a diameter of 30 cm, the first fiber-carrying bending hole 413 with a diameter of 30 cm on the first base 412 with a bottom width of 30 cm is used for placing one end of the component formed the mesh module and the fiber carrying module, the upper end of the second base 411 with a bottom width of 30 cm is provided with a second fiber-carrying bending hole 414 with a diameter of 30 cm, the second fiber-carrying bending hole 414 with a diameter of 30 cm on the second base 411 with a bottom width of 30 cm is used for placing the other end of the component formed the mesh module and the fiber carrying module, the outer edge of the bending folded shaft 415 with a diameter of 3 cm and a height of 60 cm is connected with the inner edge of the fold shaft epitaxial column 410 with a height of 50 cm and a width of 5 cm, the bending folded shaft 415 is located at a middle position of the fold shaft epitaxial column 410, the first fiber-carrying bending hole 413 with a diameter of 30 cm and the second fiber-carrying bending hole 414 with a diameter of 30 cm are connected with the bending folded shaft 415 with a diameter of 3 cm and a height of 60 cm through the fold shaft epitaxial column 410, through rotating the fold shaft epitaxial column 410, a certain angle is formed between the first fiber-carrying bending hole 413 and the second fiber-carrying bending hole 414, the first lantern ring 417 and the second lantern ring 418 are locked on the fold shaft epitaxial column 410 through a locking apparatus, a fixing plug 416 with a diameter of 3.8 cm and a height of 1.5 cm is located at the upper end surface of the bending folded shaft 415 with a diameter of 3 cm and a height of 60 cm, the part of the bending folded shaft 415 exceeding the fold shaft epitaxial column 410 has screw thread, and after the fixing plug 416 with a diameter of 3.8 cm and a height of 1.5 cm is screwed in the upper end of the bending folded shaft 415, the first fiber-carrying bending hole 413 with a diameter of 30 cm and the second fiber-carrying bending hole 414 with a diameter of 30 cm may be fixed at any angle.

In the fiber-carrying laying module, the sealing plugs 401 rotate around the bending folded shaft 402, the double-fiber channel 405 with a diameter of 5 cm may be fixed in the semicircular fiber bearing platform 406 with a diameter of 12 cm, after the sealing plugs 401 in the form of arc-shaped section symmetrically distributed at two dies of the fiber separation wall 435 with a length of 8 cm are closed, and the barrier block 400 with a length of 2 cm and a width of 1 cm is arranged on the outer end of the fiber separation wall 435 with a length of 8 cm to fix the closing parts of the sealing plugs 401. There are a total of 16 the pentagon common cavity meshes 407 with equilateral triangle section and a side length of 2 cm, and 12 circular common cavity meshes 403 with circular section and a diameter of 3 cm, the quadrangle common cavity mesh 404 is composed by 12 cavities with equilateral quadrangle section, with equilateral quadrangle section and a side length of 2.5 cm, and the pentagon common cavity mesh 408 with equilateral pentagon section and a side length of 1.5 cm is composed of three rows of 12 cavities with equilateral pentagon section. The included angle of adjacent center lines of the pentagon common cavity mesh 407, the circular common cavity mesh 403, the quadrangle common cavity mesh 404 and the pentagon common cavity mesh 408 is 90 degrees, and the pentagon common cavity mesh 407, the circular common cavity mesh 403, the quadrangle common cavity mesh 404 and the pentagon common cavity mesh 408 are connected with an inner supporter 409 in the quadrangle inner-concave shape according to an anticlockwise order in sequence. Since the section shape, size and spread pattern of each mesh are different, when the acoustic emission wave is sensed, the circular common cavity mesh 403, the quadrangle common cavity mesh 404 and the pentagon common cavity mesh 408 will respectively have different time delays and acoustic wave resonance frequencies, and the fiber separation wall 435 is the VIP plate (vacuum insulation plate).

A running method of the distributed sensing fiber acoustic emission apparatus for monitoring a hydraulic engineering safety behavior above comprises the following steps.

(1) Determine a Region to be Monitored and Select a Laying Scheme

In the embodiment, some concrete dam in the northwest is taken as the example, wherein some region to be monitored of the concrete dam is a circular area with a diameter of 100 m; due to the size of the region to be monitored and the monitoring requirement on the actual engineering, 8 pieces of GJJV tight-buffered sensing fibers with a length of 400 m are confirmed currently, the pieces of GJJV tight-buffered sensing fibers with a length of 400 m are laid in the double-fiber channel 405 with a diameter of 5 cm in pairs, the actual effective monitoring length of each sensing fiber is 350 m, and 50 m of the sensing fiber is used for connecting with other external device; since the region to be monitored is in a circular shape, 20 converter connection modules 436 will be used so as to maximumly reduce the effect of the bending loss.

(2) Equip Members and Assemble Modules

The pentagon common cavity mesh 407, the circular common cavity mesh 403, the quadrangle common cavity mesh 404 and the pentagon common cavity mesh 408 are connected with an inner supporter 409 in the quadrangle inner-concave shape according to an anticlockwise order in sequence, the sealing plugs 401 at two sides are closed by rotating the bending folded shaft 402, the barrier block 400 is passed through the upper end of the fiber separation wall 435, the closed parts of the sealing plugs 401 at the two sides are fixed, it is determined that the angles between the first fiber-carrying bending hole 413 with a diameter of 30 cm and the second fiber-carrying bending hole 414 with a diameter of 30 cm are all 18 degrees, the first base 412 with a bottom width of 30 cm and the second base 411 with a bottom width of 30 cm are rotated to form a 18-degree included angle between the first fiber-carrying bending hole 413 with a diameter of 30 cm and the second fiber-carrying bending hole 414 with a diameter of 30 cm, the fixing plug 416 with a diameter of 3.8 cm and a height of 1.5 cm is inserted into the bending folded shaft 415 with a diameter of 3 cm and a height of 60 cm, the bending folded shaft 415 is fixed, and the rest 19 parts with a 18-degree bending angle are laid by the same method;

(3) Turn on a Switch and Conduct Initial Testing

The driving power source 417 is started through controlling the controller 426, so that the mode-locked laser 418 is stimulated to generate the femtosecond laser optical frequency comb 419, the femtosecond laser optical frequency comb 419 is modulated through the pulse modulator 420, the wavelength division multiplexer 421 and the optical splitter 432, and the femtosecond laser optical frequency combs 419 of the changed Rayleigh scattering light information and the changed Brillouin scattering light information can be received and detected through the detector 425, the Rayleigh optical receiver 430, the Brillouin optical receiver 431 and the receiver 424, and are used as the initial light information reference value of the region to be monitored.

(4) Conduct Long-Term Running and Dynamic Monitoring

In the region to be monitored with a diameter of 100 m of the concrete dam, an acoustic emission signal 429 is generated when some part of the structure 428 is damaged, the acoustic emission signal transmitted through the pentagon common cavity mesh 408, the triangle common cavity mesh 407, the circular common cavity mesh 403 and the quadrangle common cavity mesh 404 may be transduced into the GJJV tight-buffered sensing fiber of the fiber-carrying laying module according to different time and frequencies, Rayleigh scattering light information and Brillouin scattering light information in the GJJV tight-buffered sensing fiber may be changed, the changed Rayleigh scattering light information and Brillouin scattering light information are collected into the concrete structure safety behavior evaluation system 427 through the controller 426, and are analyzed and compared with the result of step (3), to evaluate the damage degree and position of the structure and realize e dynamic monitoring.

The description above is only the preferable embodiment of the present invention, and it should be noted that those skilled in the art may make a plurality of improvements and decorations without departing from the principle of the present invention, and these improvements and decorations shall also fall within the protection scope of the present invention.

The invention claimed is:

1. A distributed sensing fiber acoustic emission apparatus for monitoring a hydraulic engineering safety behavior, comprising a fiber-carrying laying module and a fiber acoustic emission module, wherein the fiber-carrying laying module comprises an inner supporter, mesh modules and fiber-carrying modules, the inner supporter, the mesh modules and the fiber-carrying modules form a cylindrical shape, the cross section of the inner supporter is in a quadrangle inner-concave shape with four edges concaved, four surfaces of the inner supporter are concaved, the mesh modules having a plurality of meshes are respectively disposed in four concave surfaces of the inner supporter, and the fiber-carrying modules are arranged between every two adjacent mesh modules; and the fiber acoustic emission module comprises a driving power source, a mode-locked laser, a femtosecond laser optical frequency comb, a pulse modulator, a wavelength division multiplexer, an optical path coupler, an amplifier, a receiver, a detector, a controller, a concrete structure safety behavior evaluation system, an acoustic emission signal, a Rayleigh optical receiver, a Brillouin optical receiver, and an optical splitter, an output end of the driving power source is connected with an input end of the mode-locked laser, an input end of the driving power source is connected with an output end of the controller, the mode-locked laser is connected with the femtosecond laser optical frequency comb, the pulse modulator and the wavelength division multiplexer in sequence, an output end of the wavelength division multiplexer is respectively connected with an input end of the optical splitter and an input end of the optical path coupler, an output end of the optical splitter is respectively connected with an input end of the Rayleigh optical receiver and an input end of the Brillouin optical receiver, an output end of the Rayleigh optical receiver and an output end of the Brillouin optical receiver are connected with an input end of the controller, an output end of the optical path coupler is connected with an input end of the amplifier and an input end of the receiver, and an output end of the receiver is connected with an input end of the detector, an output end of the detector is connected with the input end of the controller, an output end of the amplifier is connected with a sensing fiber in the fiber-carrying laying module, and the output end of the controller is connected with the concrete structure safety behavior evaluation system.

2. The distributed sensing fiber acoustic emission apparatus for monitoring a hydraulic engineering safety behavior according to claim 1, wherein each of the mesh modules comprises a carrier, the carrier is provided with meshes along an axis of the sensing fiber, each carrier is provided with one of a triangle common cavity mesh, a circular common cavity mesh, a quadrangle common cavity mesh and a pentagon common cavity mesh, the shapes of the meshes the carriers are different, and the triangle common cavity mesh, the circular common cavity mesh, the quadrangle common cavity mesh and the pentagon common cavity mesh are arranged in an anticlockwise order.

3. The distributed sensing fiber acoustic emission apparatus for monitoring a hydraulic engineering safety behavior according to claim 2, wherein each of the fiber-carrying modules comprises a barrier block, sealing plugs, a double-fiber channel and a semicircular fiber bearing platform, the semicircular fiber bearing platform is connected with the carrier and is internally provided with the double-fiber channel, the double-fiber channel is internally provided with two sensing fibers, two sides of a top of the semicircular fiber bearing platform are respectively hinged with the sealing plugs, and the two sealing plugs are locked through the barrier block.

4. The distributed sensing fiber acoustic emission apparatus for monitoring a hydraulic engineering safety behavior according to claim 3, wherein the semicircular fiber bearing platform is internally provided with a fiber separation wall for separating the two sensing fibers.

5. The distributed sensing fiber acoustic emission apparatus for monitoring a hydraulic engineering safety behavior according to claim 4, wherein the fiber separation wall is a vacuum insulation panel.

6. The distributed sensing fiber acoustic emission apparatus for monitoring a hydraulic engineering safety behavior according to claim 5, further comprising a converter connection module, wherein the converter connection module comprises a first base and a second base, the first base is connected with a fold shaft epitaxial column through a first lantern ring, the second base is connected with the fold shaft epitaxial column through a second lantern ring, both the first lantern ring and the second lantern ring are provided with a locking apparatus, an upper end of the first base is provided with a first fiber-carrying bending hole, an upper end of the second base is provided with a second fiber-carrying bending hole, the fold shaft epitaxial column is provided with an inner through hole, the inner through hole is internally provided with a bending folded shaft, and an upper end surface of the bending folded shaft is provided with a fixing plug.

7. A running method of the distributed sensing fiber acoustic emission apparatus for monitoring a hydraulic engineering safety behavior according to claim 6, comprising the following steps of
first step: establishing the distributed sensing fiber acoustic emission apparatus for monitoring a hydraulic engineering safety behavior composed of the fiber acoustic emission module, the converter connection module and the fiber-carrying laying module, removing the barrier block, rotating the sealing plugs at the two sides around the bending folded shaft, arranging eight sensing fibers in four double-fiber channel in pairs, closing the sealing plugs at the two sides around the bending folded shaft, pressing a joint of the sealing plugs, passing the barrier block through an upper end of the fiber separation wall, and fixing closing parts of the sealing plugs at the two sides;
second step: placing a component formed by the mesh modules and the fiber-carrying modules in the first fiber-carrying bending hole and the second fiber-carrying bending hole at the possibly bent position of the fiber-carrying laying module, rotating the bending folded shaft according to engineering demands, so as to drive the rotation of the first base and the second base, thus forming a certain included angle between the first fiber-carrying bending hole and the second fiber-carrying bending hole, and then inserting the fixing plug into the bending folded shaft, and fixing the bending folded shaft, thus fixing the angle between the first fiber-carrying bending hole and the second fiber-carrying bending hole;
third step: opening each component in the fiber acoustic emission module, and starting the driving power source through controlling the controller, thus stimulating the mode-locked laser to generate a femtosecond laser optical frequency comb, and modulating the femtosecond laser optical frequency comb through the pulse modulator, the wavelength division multiplexer and the optical splitter; and
fourth step: an acoustic emission signal being generated when some part of a structure to be monitored is damaged, the acoustic emission signal transmitted through the pentagon common cavity mesh, the triangle common cavity mesh, the circular common cavity mesh and the quadrangle common cavity mesh being transduced into the sensing fiber of the fiber-carrying laying module according to different time and frequencies, and Rayleigh scattering light information and Brillouin scattering light information in the sensing fiber being affected, receiving and detecting the femtosecond laser optical frequency comb of the changed Rayleigh scattering light information and the changed Brillouin scattering light information through the Rayleigh optical receiver and the Brillouin optical receiver, then collecting Rayleigh and Brillouin light scattering information into the concrete structure safety behavior evaluation system through the controller for analysis and research, and evaluating and analyzing the Rayleigh and Brillouin light scattering information like damaged position and degree of the structure.

\* \* \* \* \*